United States Patent
Botten

(10) Patent No.: US 7,326,190 B2
(45) Date of Patent: Feb. 5, 2008

(54) OSTOMY POUCH AND HIGH PERFORMANCE DEODORIZING GAS FILTER ASSEMBLY THEREFOR

(75) Inventor: Ronald S. Botten, Gurnee, IL (US)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 11/376,789

(22) Filed: Mar. 16, 2006

(65) Prior Publication Data

US 2006/0271002 A1    Nov. 30, 2006

Related U.S. Application Data

(60) Provisional application No. 60/684,600, filed on May 25, 2005.

(51) Int. Cl.
    *A61F 5/44*    (2006.01)
(52) U.S. Cl. ........................... 604/333; 604/332
(58) Field of Classification Search ......... 604/327–335
    See application file for complete search history.

(56) References Cited

U.S. PATENT DOCUMENTS

| | | | |
|---|---|---|---|
| 3,759,260 A | 9/1973 | Nolan et al. | |
| 3,952,727 A * | 4/1976 | Nolan | ............ 604/333 |
| 4,460,392 A | 7/1984 | Poulsen et al. | |
| 4,516,974 A | 5/1985 | Davis | |
| 5,250,042 A | 10/1993 | Torgalkar et al. | |
| 5,250,043 A | 10/1993 | Castellana et al. | |
| 5,370,638 A | 12/1994 | Keyes | |
| 5,626,569 A | 5/1997 | Holtermann et al. | |
| 5,690,623 A | 11/1997 | Lenz et al. | |
| 6,135,986 A | 10/2000 | Leisner et al. | |
| 6,506,184 B1 * | 1/2003 | Villefrance | ............ 604/333 |

OTHER PUBLICATIONS

International Search Report from PCT/US06/011801, mailed Jul. 5, 2006.
Written Opinion of the International Searching Authority from PCT/US06/011801, mailed Jul. 5, 2006.

* cited by examiner

*Primary Examiner*—Michele Kidwell
(74) *Attorney, Agent, or Firm*—Marshall, Gerstein & Borun LLP

(57) ABSTRACT

An ostomy pouch and high-performance gas filter assembly therefore, in which the filter assembly includes an envelope defining a filter chamber containing a radial flow deodorizing filter pad. The pad's opposite faces are joined to the inner surfaces of the envelope in such a way that the periphery of the pad is fully exposed within the chamber. A first passage extends through the filter and communicates with a first opening in a wall of the envelope over which a first microporous membrane extends. A second opening extends through the opposite wall of the envelope at a distance spaced laterally from the first opening, and a second hydrophobic microporous membrane extends over the second opening. In a preferred embodiment, the filter pad is oblong in shape and has a second passage spaced laterally from the first passage and communicating with the second aperture.

8 Claims, 3 Drawing Sheets

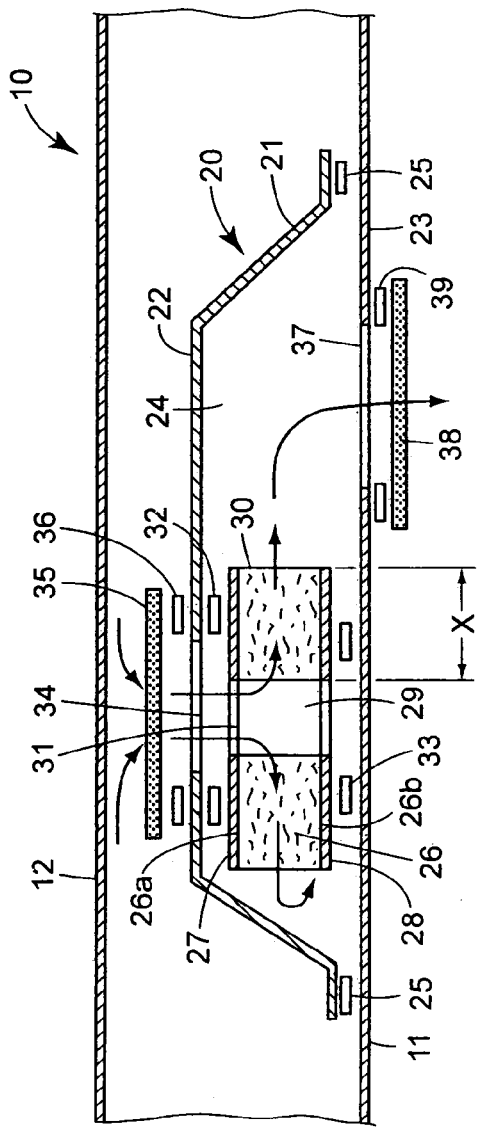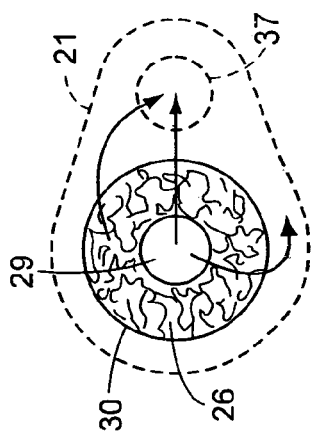

OSTOMY POUCH AND HIGH PERFORMANCE DEODORIZING GAS FILTER ASSEMBLY THEREFOR

REFERENCE TO RELATED APPLICATION

This application claims priority from U.S. Provisional Patent Application No. 60/684,600 filed May 25, 2005, as to all subject matter commonly disclosed therein.

FIELD OF THE INVENTION

It is well known to provide ostomy pouches with deodorizing gas filters so that flatus gases may be vented from the pouches to reduce or prevent ballooning and, at the same time, to deodorize the escaping gases. Typically, such a filter takes the form of disc or pad composed of fibrous elements coated with finely-divided activated carbon particles, such a disc being secured to the wall of a pouch over a vent opening. In an effort to prevent such a filter from becoming clogged and rendered ineffective by liquid and/or solid body waste material within the pouch, it has been common either to secure the filter to the outside surface of the pouch over a vent opening or to provide protection for an internally-mounted filter in the form of a porous membrane that extends over the filter that is hydrophobic and may also be oleophobic.

Filters may be of the axial flow type or the so-called radial flow type, the latter term simply meaning that the gases flow along the plane of a relatively flat filter rather than directly or axially through the thickness of that filter. A filter of the radial or planar flow type is considered desirable because it allows for the construction of a low-profile filter that nevertheless provides an extended flow path for deodorizing the flatus gases. While an extended flow path may be desirable for deodorizing purposes, it also increases the resistance to flow and thereby reduces filter performance in terms of flow rate. Protective microporous membranes also adversely affect flow rate and, to compensate for such resistance, membranes are often made larger in area than the filters that they protect. Cost then becomes an issue because the membrane material may be a substantial portion of the total cost of a deodorizing gas filter assembly and because the added production steps necessitated by including a protective membrane may further increase the cost of such an assembly.

Even when an internal filter is protected by a hydrophobic/oleophobic microporous membrane, liquid contact may still render a filter inoperative if, for example, the filter becomes saturated by water from an external source, as where an ostomate wears an ostomy pouch while taking a shower. In such a case, water may enter the filter through the vent opening in the wall of the pouch. Efforts have been made to reduce such problems by making such openings in the form of S-shape slits (see LaGro, U.S. Pat. No. 4,274,848), but it is recognized that such constructions do not completely solve the problem.

Other patents reflecting the state of the art are Nolan, et al., U.S. Pat. No. 3,759,260; Villefrance, U.S. Pat. No. 6,506,184; Lenz, U.S. Pat. No. 5,690,623; Keyes, U.S. Pat. No. 5,370,638; and Torgalkar, U.S. Pat. No. 5,250,043.

A main aspect of this invention therefore lies in providing a high-performance deodorizing gas filter assembly in which microporous hydrophobic (also selectively oleophobic) membranes protect the gas inlet located within a pouch and the gas outlet externally of the pouch. Despite the utilization of two such membranes, the filter assembly achieves high performance in terms of an air transmission rate of greater than 4.5 cc/sec, preferably greater than 7.0 cc/sec, and more preferably greater than 9.0 cc/sec, when such a filter of given area is measured at uniform pressure with a Gurley Densometer in conformance with standard test procedures (ASTM D737-96, TAPPI 460, 536 and 251, and ISO 5636/5). In terms of liquid repellency, the breakthrough pressure when subjected to a pressure increase no greater than 1.0 psi every three seconds is greater than 4.7 psi, preferably greater than 8.0 psi, and more preferably greater than 10.0 psi. All of this is achieved with an assembly having high deodorizing efficiency (i.e., greater than 250 min, preferable greater than 300 min, more preferably greater than 350 min) when tested in conformance with standardized tests for hydrogen sulfide in which 30.0 parts per million volume (ppmv) of the challenge gas is contained in a stream of nitrogen. Crack pressure values should be less than 1.0 psi, preferably less than 0.5 psi, and more preferably less than 0.3 psi.

DRAWINGS

FIG. 3 is a schematic sectional view taken along line 3-3 of FIG. 2 and showing the various components of the filter assembly in exploded condition.

FIG. 4 is a schematic view illustrating flow directions for the filter assembly.

DETAILED DESCRIPTION OF PREFERRED EMBODIMENTS OF THE INVENTION

Figure 1:
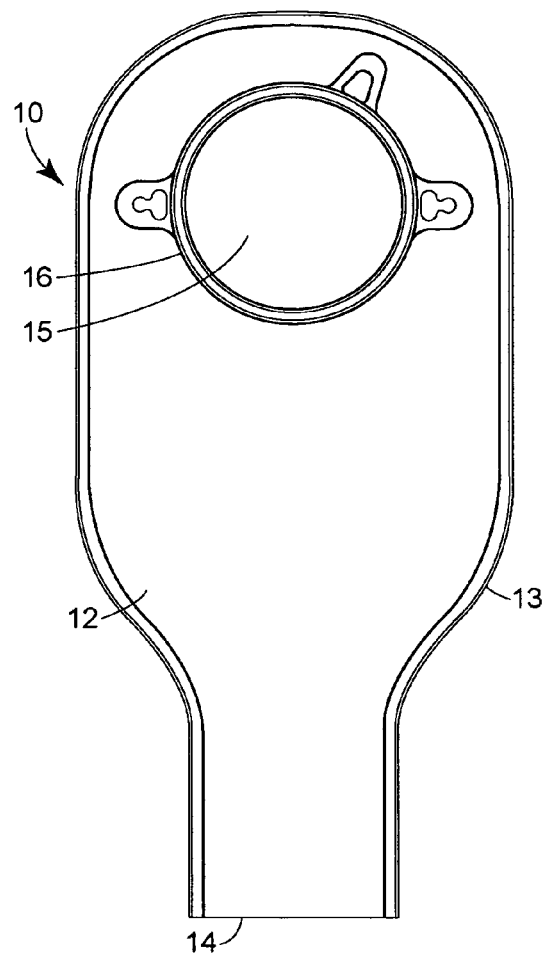
FIG. 1 is a rear (bodyside) elevational view of an ostomy pouch equipped with a filter assembly embodying the present invention.
Figure 2:
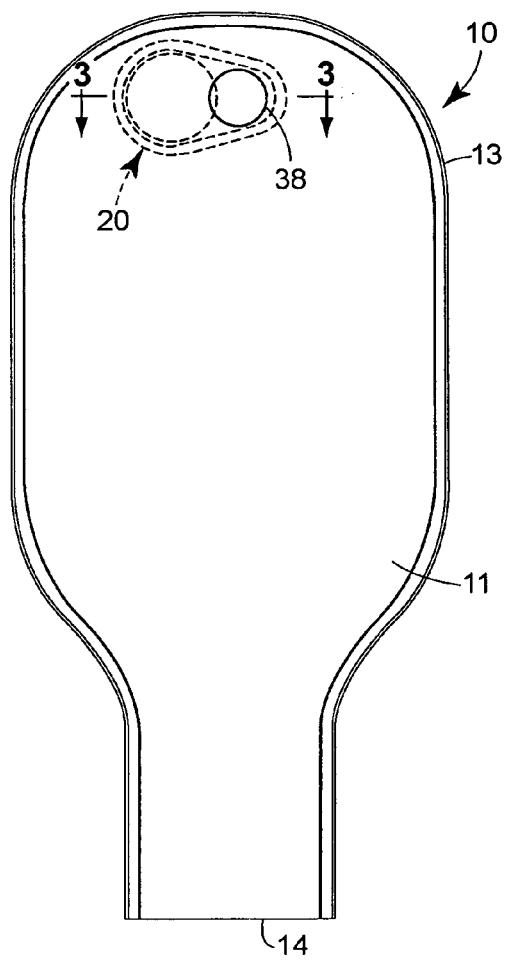
FIG. 2 is a front elevational view of the pouch.

FIGS. 1 and 2 illustrate an ostomy pouch 10 having front and rear walls 11 and 12 joined along their edges by heat sealing 13 or by any other suitable means. The pouch has a drain opening 14 that may be closed by folding and/or clamping by any variety of known closure techniques, and rear wall 12 has a stoma-receiving opening 15 surrounded by attachment means 16. In the illustration given, the pouch is one component of a so-called two-piece appliance and its attachment means takes the form of a coupling ring having a channel for releasably engaging the mating element of a faceplate coupling ring (not shown), all of which is well known in the art. Alternatively, the attachment means 16 may take the form of an adhesive ring or patch designed to adhesively engage the peristomal skin surfaces of a wearer (i.e., a one-piece appliance) or the smooth surface of a faceplate which in turn is adhesively secured to the wearer (an adhesive two-piece appliance).

FIG. 3 is an exploded and somewhat schematic sectional view showing filter assembly 20. The assembly includes an envelope 21 having first and second walls 22 and 23 of flexible thermoplastic film joined together along the edges of first wall 22 to define a filter chamber 24. In the embodiment illustrated, the parts are secured together by heat seal 25, and the second wall 23 of the envelope is actually the front wall 11 of the pouch. Alternatively, wall 23 may be a separate element that is joined to the inside surface of a pouches' front wall by any suitable attachment means.

Within chamber 24 is a generally flat, porous filter pad 26 having a pair of planar opposite faces 26a and 26b covered and sealed by gas impermeable first and second thermoplastic films 27 and 28, respectively. The filter pad has a passage 29 extending axially therethrough, that is, in a direction normal or perpendicular to the plane of the filter. While the passage is shown to be cylindrical, it may have other cross-sectional configurations than circular. The filter also has an outer peripheral surface 30 concentric with passage 29 and fully exposed within chamber 24 of the envelope. That is, the peripheral surface 30 is not occluded to any extent by wall 22 of the envelope.

Both the first film 27 and the second film 28 that cover opposite planar surfaces of the filter pad 26 have openings 31 which, in the embodiment illustrated, are shown to be in registry with passage 29 and preferably sized to match the cross-sectional configuration of that passage. However, for purposes of this invention, it is essential only that the first film 27 be provided with such an opening. Thus, the second film 28 may have no such opening, but may instead extend across the end of passage 29. A reason for providing openings 31 in both films is that at least in some instances, it may facilitate production of the filter assembly.

The outer surfaces of films 27 and 28 are sealed to the inside surfaces of envelope walls 22 and 23 by heat seals 32 and 33 or by any other suitable attachment means. It is essential that the seals 32 and 33 extend 360° about the axis of passage 29 to prevent any possibility of leakage of gas from that passage along the external surfaces of cover films 27 and 28.

The filter pad 26 may be manufactured using any of a variety of know techniques for making odor-absorbing ostomy pouch filters. One example would be a standard paper-making technique with fibers, usually polymeric, that are coated with finely-divided activated carbon using a suitable binder such as a conventional latex binder used in paper-making procedures. In general, the carbon should be finely-divided with the maximum size thereof being no greater than 100 microns, and with a size distribution in which more than one-half of the particles are less than 50 microns in size. Alternatively, the pad may be composed of carbonized viscous rayon textile, preferably arranged in a multiplicity of textile layers as disclosed in U.S. Pat. No. 6,506,184, the disclosure of which is incorporated by reference herein. For purposes of this invention, any porous odor-absorbing filter material known for use in deodorizing the flatus gases vented from an ostomy pouch is believed suitable here.

Wall 22 of envelope 21 is provided with a first aperture or opening 34 in communication with passage 29. A microporous gas-transmissible first membrane 35 extends over and across the aperture 34 and may be secured to the outer surface of wall 22 by a surrounding heat seal 36 or by any other suitable means.

In the embodiment of FIG. 3, microporous membrane 35 should be both hydrophobic and oleophobic to prevent liquids and solids from entering passage 29 from the interior of pouch 10. A number of materials suitable for such use are commercially available, one being "Gore-Tex", a microporous polytetrafluoroethylene membrane marketed by W. L. Gore & Associates, Newark, Del. While different porosities for such a membrane may be suitable, it is preferred that the membrane have a pore size allowing passage through the membrane only of particles having a maximum dimension smaller than three microns, and more preferably two microns or less. Another material suitable for use as a microporous hydrophobic and oleophobic membrane is available from Millipore Corporation, Bedford, Mass., and is disclosed in U.S. Pat. No. 4,778,601 incorporated herein by reference. Such a membrane is composed of microporous ultra high molecular weight polyethylene.

Wall 23 of the envelope 21 is provided with a second aperture or opening 37 spaced laterally from the first aperture 34 of wall 22. More specifically, in the embodiment of FIG. 3, the aperture 37 is located laterally beyond the outer peripheral surface 30 of filter pad 26. A second microporous membrane 38 extends across opening 37 and is secured to the outer surface of wall 23 by a surrounding heat seal 39 or by any other suitable sealing and attachment means. The material selected for membrane 38 may be the same as that used for membrane 35, such membrane being both hydrophobic and oleophobic. However, it is also believed suitable in the embodiment of FIG. 3 to use a microporous membrane that is hydrophobic but does not have oleophobic properties. The reason is that membrane 38 functions to protect chamber 24 and the filter therein against exposure to water from an external source (e.g., a shower), and for such purposes oleophobic properties may be unnecessary.

The directions of gas flow are indicated by arrows in FIGS. 3 and 4. Flatus gases from the interior pouch 10 pass through protective microporous membrane 35 and enter passage 29 of the annular filter pad 26. Filter 26 is of the radial flow type, so such gases then flow from passage 29 radially outwardly, that is, outwardly along the plane of the filter. The dimension of the flow path through the filter is represented by the letter "x" in FIGS. 3 and 4. The length of that flow path may be increased or decreased as desired in order to achieve optimum filtering efficiency. After leaving filter 26, the deodorized gases pass outwardly through outlet opening 37 and microporous membrane 38.

It is to be noted that the gases may escape from the filter in any radial or planar flow path extending 360° about the filter. This is schematically depicted in FIG. 4 where only the annular filter is shown in solid lines. Because the outer peripheral surface 30 of the filter is fully exposed within chamber 24 and is not occluded to any extent by envelope wall 21, the gases may pass to outlet opening 37 by following either a direct route or by any other route over the range of 360° as indicated by the arrows.

Figure 5:
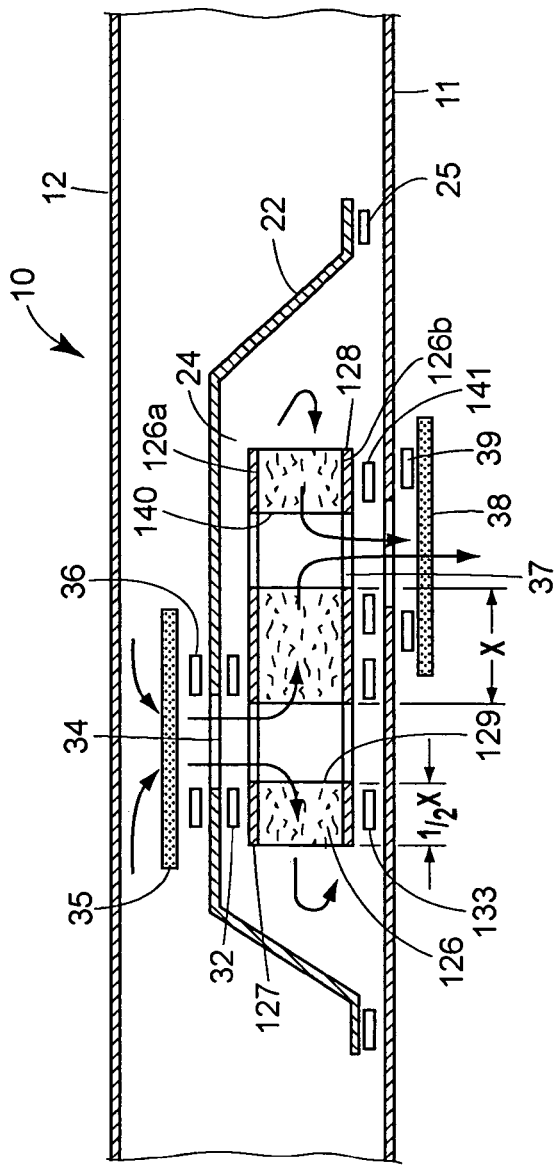
FIG. 5 is an exploded cross-sectional view similar to FIG. 3, but illustrating a second embodiment of the invention.

The embodiment of FIG. 5 is similar to that of FIG. 3 except for differences in the construction of the filter. Hence, the numerals used for most of the parts are the same as those used in FIG. 3, and discussion of the composition, construction, and arrangement of like parts will not be repeated.

Figure 6:
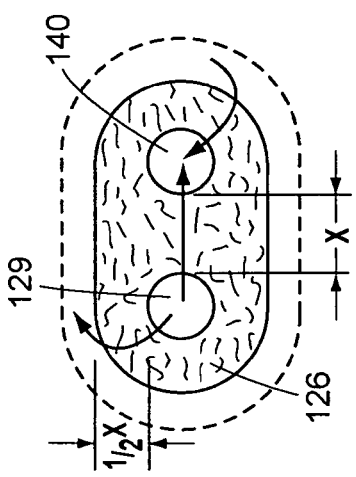
FIG. 6 is a schematic view illustrating flow direction and filtering dimensions for the assembly of FIG. 5.

Filter pad 126 is composed of the same filtering and odor-absorbing material described for filter pad 26. Its planar opposite faces 126a and 126b are similarly provided with gas impermeable cover films 127 and 128 secured to opposite faces of the pad, and annular heat seals 133 and 141 then join the cover films to the wall 11 of the envelope. However, unlike the earlier pad, pad 126 is oblong or oval in outline and has two flow passages 129 and 140, the latter being aligned with the second aperture (outlet opening) 37. As before, flatus gases entering chamber 24 flow axially into passage 129 and then radially outwardly over a range of 360° about the axis of passage 129. The most direct route to the second passage 140 is represented by dimension "x" in FIGS. 5 and 6 which, for purposes of comparison, is the same distance "x" shown in FIGS. 3 and 4. It will be noted, however, that for an angular distance of 180° about each cylindrical passage 129 and 140 of the oblong pad 126, the radial dimension is shown to be only ½ "x". Nevertheless, the shortest flow path through the filter pad from the first aperture (inlet opening) 34 to the second aperture (outlet opening) 37 remains "x" because any gases exiting the filter through the ½ "x" dimension must again re-enter the filter, now flowing radially inwardly, for another distance of ½ "x", to enter the second passage 140. In FIGS. 5 and 6 it will be noted that the shortest dimension from each of the passages 129 and 140 to the periphery of the filter is at least ½ "x" because of the oval symmetry of the filter but, whether the filter is symmetrical or non-symmetrical (e.g. pear-shaped in outline), the essential requirement is that the sum of the shortest distances between the respective passages and the periphery of the filter be no less than "x".

Figure 7:
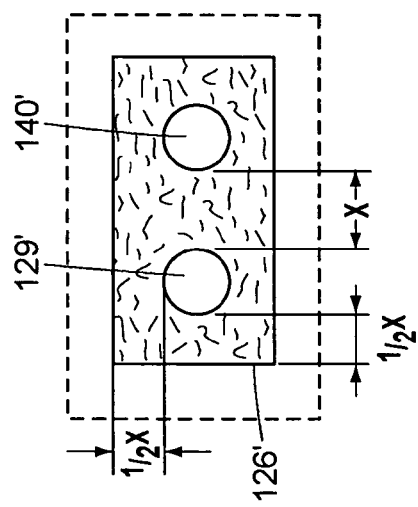
FIG. 7 depicts a modification of the assembly shown in FIGS. 5 and 6.

FIG. 7 is a schematic view similar to FIG. 6, but showing that an oblong filter pad 126' might be rectangular rather than oval in shape. The operation is otherwise identical with the minimum (i.e. direct) flow path from passage 129' to 140' still being "x". The passages might be of generally circular cross-section as in FIG. 6 or the may be of other cross-sectional shapes. Square cross-sections are depicted in FIG. 7. Whatever the cross-sectional shape selected, the shortest flow path between each passage 129' and 140' and the outer periphery of the filter pad is shown in FIG. 7 to be at least ½ "x". Thus, the sum of the shortest distances to the pad's outer periphery from the two passages considered together should be at least "x".

The embodiment of FIG. 7 might be advantageous to that of FIG. 6 for production reasons, since the filter 126' might be cut from stock without wastage. Also, the embodiments of FIGS. 5 to 7 are believed to have some advantages over the embodiment of FIGS. 3 and 4 in terms of ease of production and because the oblong (generally rectangular, or oval) shape of the filter allows the filter to perform a further function as a uniform spacer between the walls 22 and 23 of the envelope, thereby preventing or reducing the possibility that such walls might directly contact or block against each other.

While it is essential that the filters of the embodiments so far described be of the radial or planar flow type, it is not required (although perhaps preferable) that the filters be located within the pouch 10. Thus, referring to the embodiment of FIG. 3, filter 26 and its envelope 21 might be located outside the pouch 10 with the filter pad 26 positioned within the envelope at the second aperture (outlet opening) 37. In such a case, the first aperture 35 would function as the inlet opening. Both apertures would again be protected by microporous hydrophilic membranes, but in such an arrangement it would be the second membrane 38 at the second aperture (inlet) 37 that would be required to be oleophobic as well as hydrophobic, whereas the first membrane 35 at the first aperture (outlet) 34 might only be hydrophobic. In such an embodiment, the gas flow through the filter 26, while radial, would be just the reverse of what is shown in FIG. 3, that is, the flow would be radially inwardly from the periphery rather than radially outwardly from the filter's central passage.

Similarly, the envelope 22 shown in FIG. 5 might be located externally of the pouch 10 but, as shown by the arrows in that figure, the flow of gasses would continue to be first in a radially outward direction from the first passage and then in a radially inward direction into the second passage. The result, in each and all of the embodiments, is a filter assembly which, despite its radial flow operation (which involves an extended flow path in relation to conventional axial-flow ostomy pouch filters), and despite the provision of two protective membranes for such filter, may nevertheless be of distinctively high-performance measured in terms of minimum gas transmission rate, liquid repellency or hold out, and deodorization capability. Allowing for differences in the compositions and dimensions of the filters and the inlet and outlet membranes, it is found that the assemblies disclosed herein are capable of air transmission rates greater than 4.5 cc/sec., preferably greater than 7.0 cc/sec., and more preferably greater than 9.0 cc/sec. when measured in conformance with standard procedures such as ASTM D737-96, TAPPI 460, 536 and 251, and ISO 5636/5. In such a test, a Gurley Densometer (Model 4110) is used to measure porosity or air-resistance of sheet-like materials. The test measures the time for the flow of a standard volume of air (e.g. 100 cc) to pass through a standard area (1 sq. in) under uniform pressure. More specifically, an air-filled cylinder is pressurized by a 20 oz. piston and, when the air is released, timers automatically measure the time for 100 cc of air to pass through the filter. Data is generally captured in seconds and converted into measured flow rates of cc/sec of air.

Further, such a filter assembly embodying this invention is capable of liquid hold-out or repellency, of greater than 4.7 psi, preferably greater than 8.0 psi, and more preferably greater than 10 psi when tested to measure the liquid pressure at which liquid will first break through such a filter. In such a procedure, the specific liquid used is de-ionized water, soap and dye (blue in color). The filter assembly is clamped over a liquid chamber such that the filter assembly is visible. Liquid pressure is increased under the filter assembly at a rate no greater than 1.0 psi every 3 seconds until breakthrough is visually observed (at a distance of 12 in) on the filter surface opposite the liquid chamber. The pressure at which breakthrough is first visually observed is then recorded as the breakthrough pressure.

It has also been found that crack pressure, that is, the minimum pressure needed to produce air flow through the filter assemblies of this invention, should be less than 1.0 psi, preferably less than 0.5 psi, and more preferably less than 0.3 psi.

As to deodorizing capability, the assemblies of this invention withstand a transmission of odors, when measured using hydrogen sulfide gas in a nitrogen stream, for periods greater than 250 min, preferably greater than 300 min, and more preferably greater than 350 min using hydrogen sulfide as the challenge gas. Such a procedure is commonly used to evaluate the performance of activated carbon ostomy filters for the removal of a challenge gas (hydrogen sulfide) from a stream of nitrogen. A nitrogen stream containing 30.0 ppmv hydrogen sulfide is passed through an ostomy filter until a 1.0 ppmv breakthrough of hydrogen sulfide is detected. After passing through the ostomy filter, the nitrogen stream is analyzed for the presence of the challenge gas every 12 minutes. The time to reach the stated post-filtering hydrogen sulfide gas concentration level is then recorded. Proper nitrogen flow of 250 cc/min is verified prior to each ostomy filter test, and the nitrogen flow is analyzed for the presence of the challenge gas by means of gas chromatography with a flame photometric detector (FPD).

While radial-flow ostomy pouch filters have been known in the past, including assemblies having protective microporous membranes therefor, applicant is unaware of any such filter assembly with dual membranes that has been marketed, or is being marketed, achieving both the air transmission levels and the hold-out levels of the filter assemblies of this invention, much less any prior filter assembly that also has the deodorizing capabilities and the crack pressure characteristics described above.

The term "radial flow" has been used throughout this application to refer to the flow through a flat ostomy filter in directions parallel with its planar faces, in contrast to a flow direction directly through the thickness of that filter which is considered as axial flow. Thus, "radial" refers to a direction toward or away from a passage extending through the thickness of the filter and is not limited to filters in which such passages are circular in cross-section. As disclosed above, such passages may be of square cross section or any other suitable cross-section.

I claim:

1. An odor-absorbing gas filter assembly for body waste collection pouches, comprising an envelope having first and second walls of flexible thermoplastic film joined together along edges to define a filter chamber; a porous radial flow filter pad with activated carbon therein located within said chamber and having a pair of planar opposite faces; said pad having a passage extending therethrough from one face to the other and having an outer peripheral surface fully exposed within said filter chamber; said opposite faces being joined respectively to the inner surfaces of the first and second walls of said envelope to block the axial flow of gases through said filter pad; said first wall of said envelope having a first aperture communicating with said passage; a first microporous gas-transmissible membrane of hydrophobic material sealed to said first wall about said first aperture and extending over said first aperture to prevent liquids from entering said passage and said filter pad; said second wall of said envelope having a second aperture spaced laterally from said first aperture; and a second microporous gas-transmissible membrane of hydrophobic material sealed to said second wall about said second aperture and extending over said second aperture to prevent liquids external to said envelope from entering said chamber; said filter pad being oblong in shape with opposite end portions; said passage constituting a first passage located in one of said end portions of said pad; said pad also having a second passage therethrough located in the opposite end portion of said pad; said first and second passages being spaced a predetermined distance x from each other; said second passage communicating with said second aperture and said second membrane; said passages together being spaced from said peripheral surface of said pad a combined distance no less than distance x.

2. An odor-absorbing gas filter assembly for body waste collection pouches, comprising an envelope having first and second walls of flexible thermoplastic film joined together along edges to define a filter chamber; a porous radial flow filter pad with activated carbon therein located within said chamber and having a pair of planar opposite faces; said pad having a passage extending therethrough from one face to the other and having an outer peripheral surface fully exposed within said filter chamber; said opposite faces being joined respectively to the inner surfaces of the first and second walls of said envelope to block the axial flow of gases through said filter pad; said first wall of said envelope having a first aperture communicating with said passage; a first microporous gas-transmissible membrane of hydrophobic material sealed to said first wall about said first aperture and extending over said first aperture to prevent liquids from entering said passage and said filter pad; said second wall of said envelope having a second aperture spaced laterally from said first aperture; and a second microporous gas-transmissible membrane of hydrophobic material sealed to said second wall about said second aperture and extending over said second aperture to prevent liquids external to said envelope from entering said chamber; one of said faces of said pad being covered by a gas-impermeable first film having an opening communicating with said passage and the other of said faces being covered by a gas-impermeable second film; said first aperture of said first wall of said envelope communicating with said first opening of said first film.

3. The assembly of claim 2 in which said filter pad is oblong in shape with opposite end portions; said passage constituting a first passage located in one end portion of said pad; said pad also having a second passage therethrough located in the opposite end portion of said pad; said first and second passages being spaced a predetermined distance x from each other; said second passage communicating with said second aperture and said second membrane; said passages together being spaced from said peripheral surface of said pad a combined distance no less than distance x.

4. The assembly of claim 3 in which said oblong filter pad is generally oval in shape.

5. The assembly of claim 3 in which said oblong filter pad is generally rectangular in shape.

6. A body waste collection pouch having front and rear walls joined together along their peripheral edges; said rear wall having a stoma-receiving opening externally surrounded by attachment means for securing said pouch to a wearer; an odor-absorbing gas filter assembly within said pouch comprising an envelope having first and second walls of flexible thermoplastic film joined together along edges to define a filter chamber; a porous radial flow filter pad containing activated carbon located within said chamber and having a pair of planar opposite faces; said pad having an inlet passage extending therethrough from one face to the other and having an outer peripheral surface fully exposed within said filter chamber; one of said faces being covered by a gas-impermeable first film having an opening communicating with said passage and the other of said faces being covered by a gas-impermeable second film; said first and second films being sealed respectively to the inner surface of the first and second wall of said envelope; said first wall of said envelope having an inlet opening communicating with said opening of said first film and said inlet passage; a microporous gas-transmissible inlet membrane of hydrophobic and oleophobic material sealed to said first wall about said inlet opening and extending over said inlet opening to prevent liquids and solids from entering said inlet passage; said second wall of said envelope having an outlet opening spaced laterally from said opening of said first wall; and a microporous gas-transmissible outlet membrane of hydrophobic material sealed to said second wall about said outlet opening and extending over said outlet opening to prevent liquids external to said envelope from entering said chamber; said filter pad being oblong in outline and having opposite end portions; said inlet passage being located in one of said end portions; said pad also having an outlet passage therethrough located in the end portion opposite from said one end portion; said inlet and outlet passages being spaced a predetermined distance x from each other; said outlet passage communicating with said outlet opening and said outlet membrane; said inlet and outlet passages being spaced from said peripheral surface of said pad a minimum combined distance no less than x.

7. The pouch of claim 6 in which said oblong filter pad is generally oval in shape.

8. The pouch of claim 6 in which said oblong filter pad is generally rectangular in shape.

* * * * *